(12) United States Patent  (10) Patent No.: US 9,201,068 B2
Suni et al.  (45) Date of Patent: Dec. 1, 2015

(54) BIOELECTRONIC TONGUE FOR FOOD ALLERGY DETECTION

(75) Inventors: Ian Ivar Suni, Potsdam, NY (US); Yin Huang, Toronto (CA); Stephanie Ann Caswell Schuckers, Canton, NY (US)

(73) Assignee: CLARKSON UNIVERSITY, Potsdam, NY (US)

( * ) Notice: Subject to any disclaimer, the term of this patent is extended or adjusted under 35 U.S.C. 154(b) by 0 days.

(21) Appl. No.: 12/584,341

(22) Filed: Sep. 3, 2009

(65) Prior Publication Data

US 2010/0222224 A1  Sep. 2, 2010

Related U.S. Application Data

(60) Provisional application No. 61/136,398, filed on Sep. 3, 2008, provisional application No. 61/270,934, filed on Jul. 15, 2009.

(51) Int. Cl.
*G01N 33/53* (2006.01)
*G01N 33/543* (2006.01)

(52) U.S. Cl.
CPC ..... *G01N 33/5438* (2013.01); *B01J 2219/0074* (2013.01); *B01J 2219/00605* (2013.01); *B01J 2219/00725* (2013.01)

(58) Field of Classification Search
None
See application file for complete search history.

(56) References Cited

U.S. PATENT DOCUMENTS

| | | | | |
|---|---|---|---|---|
| 6,441,142 | B1 * | 8/2002 | Burks et al. | 530/387.9 |
| 2002/0076804 | A1 * | 6/2002 | Sheppard et al. | 435/287.1 |
| 2003/0013130 | A1 * | 1/2003 | Charych et al. | 435/7.1 |
| 2003/0092074 | A1 * | 5/2003 | Ezaki | 435/7.9 |
| 2003/0138845 | A1 * | 7/2003 | Li et al. | 435/7.1 |
| 2004/0189311 | A1 * | 9/2004 | Glezer et al. | 324/444 |
| 2005/0252777 | A1 * | 11/2005 | Li | 204/600 |
| 2006/0029978 | A1 * | 2/2006 | O'Neill et al. | 435/7.1 |
| 2006/0108236 | A1 * | 5/2006 | Kasielke et al. | 205/792 |
| 2006/0134657 | A1 * | 6/2006 | Hodko et al. | 435/6 |
| 2006/0275786 | A1 * | 12/2006 | Long et al. | 435/6 |
| 2007/0117217 | A1 * | 5/2007 | Lal et al. | 436/513 |
| 2007/0231926 | A1 * | 10/2007 | Ikeda | 436/526 |
| 2008/0171323 | A1 * | 7/2008 | Banchereau et al. | 435/6 |

* cited by examiner

*Primary Examiner* — Jacob Cheu
(74) *Attorney, Agent, or Firm* — Gerow D. Brill

(57) ABSTRACT

The present invention is directed to a method and apparatus that satisfies the need for a bioelectronic tongue for food allergy detection. The method of detecting concentration of food allergen incorporates antibodies into an electronic tongue to create a bioelectronic tongue. Additionally the method uses impedance, capacitance, and/or other related electrochemical methods for detecting analyte in complex media. Furthermore the method additionally includes methods to subtract out non-specific interactions. The method also subtracts non-specific interactions. The device/apparatus is a Bioelectronic Tongue for detecting allergen in diluted food samples. The device includes: a sensor array; an impedance or capacitance analyzer; a preprocessor; a feature extractor; a pattern recognizer; and an output device indicating an allergen concentration. In order to implement the method of detecting food allergens on a bioelectronic tongue a computer readable medium containing an executable program is used for performing the analysis of a food sample. The executable program performs the acts of: preprocessing data from an impedance analyzer; extracting a feature pattern; recognizing a pattern of features of data representing a concentration of food allergen contained is the food sample; and outputs allergen concentration data.

26 Claims, 6 Drawing Sheets

BIOELECTRONIC TONGUE FOR FOOD ALLERGY DETECTION

CROSS REFERENCE

This application is related to Provisional Application No. 61/136,398, dated 3 Sep. 2008 by Ian Ivar Suni and Stephanie A. Shuckers and Provisional Application No. 61/270,934 dated 15 July by Ian Suni and Matthew Souva. Both applications are hereby incorporated in their entirety herein by reference.

GOVERNMENT CONTRACT SUPPORT

The research for this application was supported by Contract Number US Army W911NF-05-1-0339.

FIELD OF THE INVENTION

The field of the invention is the detection food allergens in particular the detection food allergens using a bioelectronic tongue for food allergy detection.

BACKGROUND OF INVENTION

Food allergens, which are typically proteins or glyco-proteins of size 10-70 kDa, present a serious public health problem, in part because allergy immunotherapy is currently unavailable. Most food allergies are caused by crustaceans, fish, eggs, peanuts, milk, tree nuts, soybeans, or gluten-containing cereals. Food allergies are especially common among children, afflicting about 6-8% of children less than three years of age. (See S. A. Bock, "Prospective appraisal of complaints of adverse reactions to foods in children during the first three years of life," *Pediatrics* 79, 683 (1987) hereby incorporated herein by reference.) Peanuts are considered one of the most dangerous food allergens, with severe anaphylactic reactions causing over 100 fatalities in the USA alone each year. (See W. Burks, G. A. Bannon, S. Sicherer and H. A. Sampson, "Peanut-induced anaphylactic reactions," *Inter. Arch. Allergy Immunol.* 119, 165 (1999) hereby incorporated by reference.) Exposure to peanut allergens is often inadvertent, arising from ingestion of foods not believed to contain peanuts. (See T. J. Furlong, J. DeSimone and H. Sicherer, "Peanut and tree nut allergic reactions in restaurants and other food establishments," *J. Allergy Clin. Immunol.* 108, 867 (2001) hereby incorporated by reference.) Nine allergens within peanuts have been identified, Ara h1 to Ara h 8, and peanut oleosin. (See G. W. Palmer, D. A. Dibbern, A. W. Burks, G. A. Bannon, S. A. Bock, H. S. Porterfield, R. A. McDermott and S. C. Dreskin, "Comparative potency of Ara h1 and Ara h 2 in immunochemical and functional assays of allergenicity," *Clin. Immunol.* 115, 302 (2005) and 5. A. Barre, J. P. Borges, R. Culerrier, and P. Rouge, "Homology modeling of the major peanut allergen Ara h 2 and surface mapping of IgE-binding epitopes," *Immunol. Lett.* 100, 153 (2005) both hereby incorporated by reference.) Ara h 1 and Ara h 2 are widely described as the most important allergens, although this has been disputed.

Current methods for detecting peanut proteins are based on enzyme linked immuno-sorbent assays (ELISA), (See A. Pomes, R. M. Helm, G. A. Bannon, A. W. Burks, A. Tsay and M. D. Chapman, "Monitoring peanut allergen in food products by measuring Ara h 1," *J. Allergy Clin. Immunol.* 111, 640 (2003); M. L. Nogueira, R. McDonald and C. Westphal, "Can commercial peanut assay kits detect peanut allergens?," *J. AOAC Int.* 87, 1480 (2004); D. A. Schmitt, H. Cheng, S. J. Maleki and A. W. Burks, "Competitive inhibition ELISA for quantification of Ara h 1 and Ara h 2, the major peanut allergens," *J. AOAC Int.* 87, 1492 (2004) and M. Kiening, R. Niessner, E. Drs, S. Baumgartner, R. Krska, M. Bremer, V. Tomkies, P. Reece, C. Danks, U. Immer and M. G. Weller, "Sandwich immunoassays for the determination of peanut and hazelnut traces in foods," *J. Agric. Food Chem.* 53, 3321 (2005) all of which are hereby incorporated herein by reference) which are time consuming, require trained personnel, are difficult to automate and miniaturize, and are not fully standardized. (See A. L. Ghindilis, P. Atanasov, M. Wilkins and E. Wilkins, "Immunosensors: Electrochemical sensing and other engineering approaches," *Biosens. Bioelectron.* 13, 113 (1998) herby incorporated by reference. For these reasons, ELISA is unlikely to be practical for point-of-use applications, where portable and immediate detection is needed, so alternative immunosensors to ELISA are considered highly desirable. (See I. Mohammed, W. M. Mullett, E. P. C. Lai and J. J. Yeung, "Is biosensor a viable method for food allergen detection?" *Anal. Chim. Acta* 444, 97 (2001) hereby incorporated herein by reference.)

Biosensors for food allergens have been reported using capillary electrophoresis/laser-induced fluorescence, (See M. T. Veledo, M. de Frutos and J. C. Diez-Masa, "Analysis of trace amounts of bovine β-lactoglobulin in infant formulas by capillary electrophoresis with on-capillary derivatization and laser-induced fluorescence detection," *J. Separ. Sci.* 28, 941 (2005) hereby incorporated herein by reference) liquid chromatography/mass spectrometry, (See K. J. Shefcheck and S. M. Musser, "Confirmation of the allergenic peanut protein, Ara h 1, in a model food matrix using liquid chromatography/tandem mass spectrometry (LC/MS/MS)," *J. Agric. Food Chem.* 52, 2785 (2004) hereby incorporated herein by reference) and electrochemical impedance spectroscopy (EIS). (See H. Huang, P. Ran and Z. Liu, "Impedance sensing of allergen-antibody interaction on glassy carbon electrode modified by gold electrodeposition," *Bioelectrochemistry* 70, 257 (2007) hereby incorporated herein by reference.)

Electrochemical impedance spectroscopy involves application of a small sinusoidal AC voltage probe to an electrode and determination of the current response. Electrochemical impedance spectroscopy has been previously employed as a transduction method for biological recognition, and detection limits have been reported in the nM to pM range for impedance biosensors. However, the use of impedance biosensors for detecting food allergens has not been reported. One disadvantage of many biosensor methods, including electrochemical impedance spectroscopy, is that non-specific interactions can venerate false positives. In other words, species other than the desired analyte, such as peanut protein, can also interact with the surface-immobilized antibody.

This specificity shortcoming can be overcome by using a bioelectronic tongue, which is an array of antibody-coated electrodes whose response to real food matrices is analyzed with signal processing algorithms to separate the electronic signature of peanut protein from that of interfering species. The bioelectronic tongue can be distinguished from an electronic tongue by the incorporation of biomolecules, such as antibodies, as will be discussed in detail below. The response of each sensor to a specific sample is converted to a digital time-series for each sensor. The array of sensors results in a numerical matrix that must be analyzed to unearth the pattern. The pattern analysis protocol includes signal preprocessing to prepare the data, dimensionality reduction to extract relevant features from the data, and classification through automated classifiers that could include clustering, k-nearest neighbor classification, neural networks, and regression.

SUMMARY OF THE INVENTION

The present invention is directed to a method and apparatus that satisfies the need for a bioelectronic tongue for food allergy detection.

The method comprises a process for determining a concentration of a food allergen begins with providing a providing a plurality of diluted test samples and applying these test samples to a sensor array. An impedance analyzer is used to create an electrical signal based on the contents of each sample and is representative of the samples. This electrical signal is preprocessed to determine baseline data so that baseline adjustment and drift compensation may be performed. A feature pattern is extracted from the baseline data. Feature selection includes mapping of dimensional feature space into a projection of features ordered by variability.

The process of recognizing a pattern of features of the data representing a concentration of food allergen contained in the test samples is the final step in detecting allergens. The acts of pattern recognition include a training set, a test set and a validation set.

The training set includes creating a model and selecting thresholds. The training set is an iterative process where weights/models are updated to minimize classification errors.

The method test set verifies that the model will generalize to an unseen set of data.

The validation set uses cross-validation, where a small set is withheld for validation while the remaining data is used for training/testing with the validation process being repeated many times (100× or more) repeatedly on small subsets of performance on an unseen data set.

Once determined, the allergen concentration value is outputted on a display device so that a user knows the level of allergen in the test sample.

The method of detecting concentration of food allergen incorporates antibodies into an electronic tongue to create a bioelectronic tongue. Additionally the method uses impedance, capacitance, and/or other related electrochemical methods for detecting analyte in complex media. Furthermore the method additionally includes methods to subtract out non-specific interactions. The method also subtracts non-specific interactions.

The device/apparatus is a Bioelectronic Tongue for detecting allergen in diluted food samples. The device includes: a sensor array; an impedance or capacitance analyzer; a preprocessor; a feature extractor; a pattern recognizer; and an output device indicating an allergen concentration.

The sensor array further includes a plurality of locations for diluted food or other samples. The preprocessor preprocesses baseline data. The feature extractor maps a dimensional feature space into a projection of features ordered by variability. The pattern recognizer includes a training set, a test set and a validation set. The output device s selected from the group consisting of LED display, LCD display, OCLD display, CRT display and indicator lamp.

In order to implement the method of detecting food allergens on a bioelectronic tongue a computer readable medium containing an executable program is used for performing the analysis of a food sample. The executable program performs the acts of: preprocessing data from an impedance analyzer; extracting a feature pattern; recognizing a pattern of features of data representing a concentration of food allergen contained is the food sample; and outputs allergen concentration data.

The preprocessing data includes baseline data so that baseline adjustment and drift compensation may be performed. The feature selection includes a mapping of dimensional feature space into a projection of features ordered by variability. The pattern recognition portion includes a training set, a test set and a validation set.

The training set includes creating a model and selecting thresholds. The training set is an iterative process where weights/models are updated to minimize classification errors. The test set verifies that said model will generalize to an unseen set of data. The validation set uses cross-validation, where a small set is withheld for validation while the remaining data is used for training/testing with said validation process is repeated many times (100× or more) repeatedly on small subsets of performance on an unseen data set. The outputting portion outputs the allergen data to a display device.

As discussed above, even though peanut allergens have been the main focus of this application, the concepts and techniques presented are applicable to other food allergens. The technology may be applied to other allergens such as β-lactoglobulin, which is believed to be the main allergenic protein in cow's milk, and Tri a Bd 27K, which is believed to be the main allergenic protein in wheat. Therefore this application is not limited to peanut allergens.

BRIEF DESCRIPTION OF THE DRAWINGS

These and other features, aspects, and advantages of the present invention will become better understood with regard to the following description, appended claims, and accompanying drawings where:

FIG. 5 illustrates the dependence of the fit impedance parameters on the concentration of peanut protein Ara h 1.

DETAILED DESCRIPTION

Figure 1:
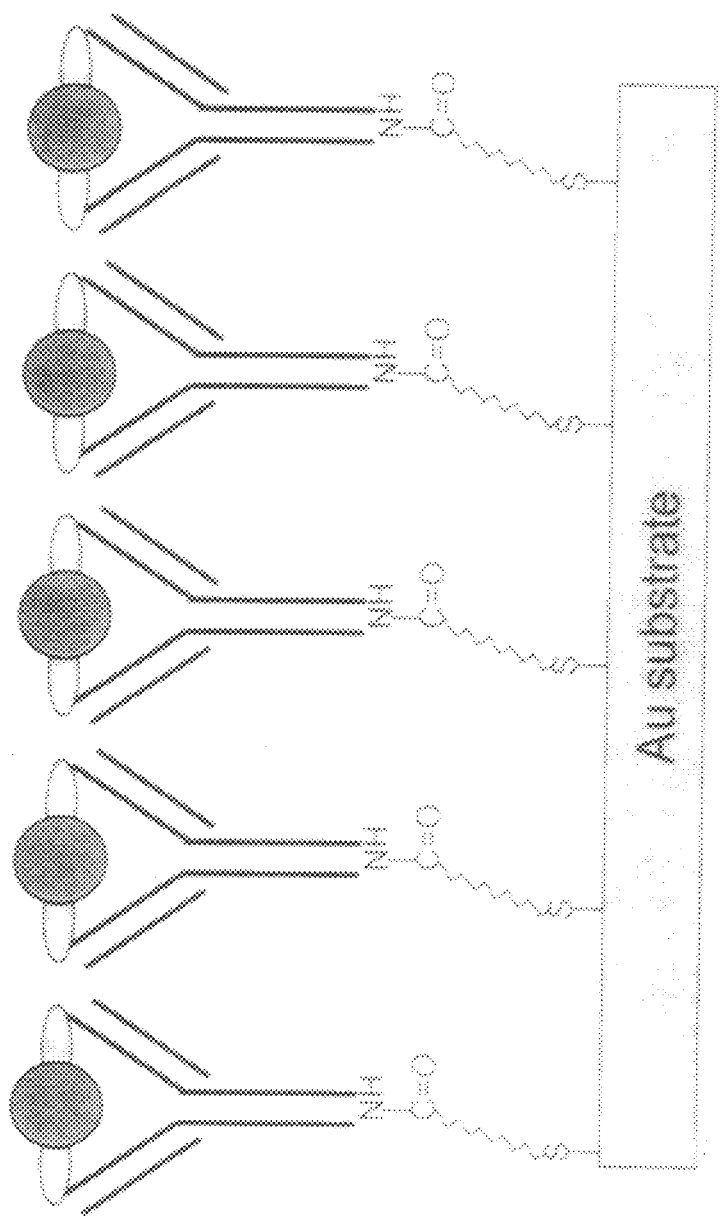
FIG. 1 illustrates detection scheme for peanut proteins Ara h 1, which can be translated to detection of other food allergens.
Figure 2:
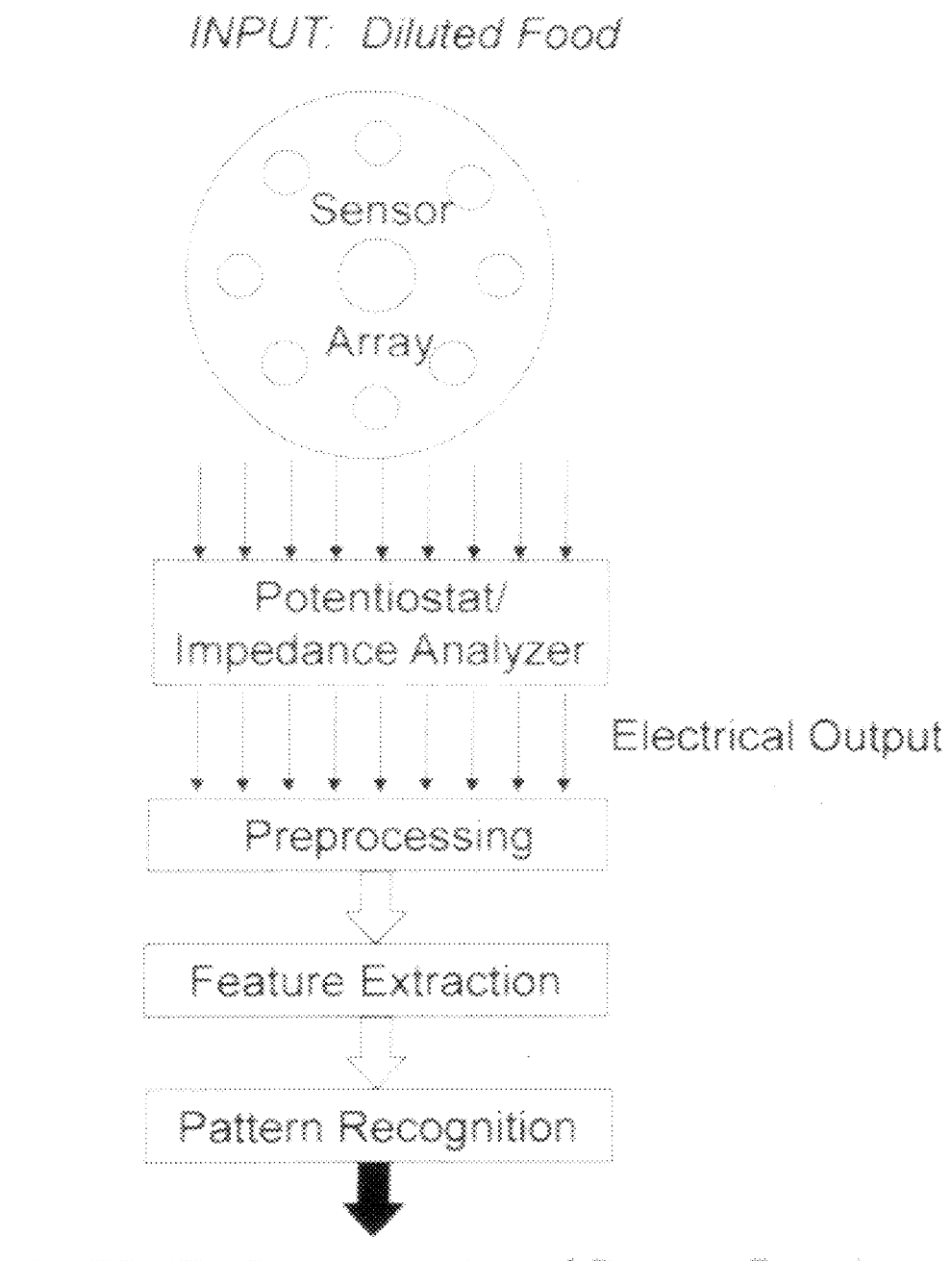
FIG. 2 illustrates the process flow of detecting a food allergen using a bioelectronic tongue.

FIG. 1 represents the desired biomolecular recognition process between an antibody and a food protein allergen that can occur at an individual electrode within the bioelectronic tongue. FIG. 2 illustrates the flow of detecting a food allergen from a sample with a bioelectronic tongue, which contains many such electrodes. The first step is providing a diluted food sample 10. The reason for diluting the sample will be understood in the detailed discussion below. The sample(s) are made part of a sensor array 12. The samples are detected by a potentiostat/impedance analyzer which provides an electrical output 14 to a preprocessing portion 14. The feature extraction 16 selects data from the output of the preprocessing portion 14. The output of feature extraction 18 portion provides data to a pattern recognition portion 20 that determines the concentration of a food allergen within the sample. The concentration of the allergen of interest may be displayed on a display device (not shown).

Overview of Electronic Tongue Methods:

The electronic tongue is an established technology that combines a multi-electrode array of only partly selective sensors with pattern recognition algorithms that separate the "true" signal from the detailed sensor response to complex, real-world samples that typically contain interfering species. (For an overview of electronic research, see F. Winquist, C.

Krantz-Rulcker and I. Lundstrom, "Electronic tongues," *MRS Bullet.* 29, 726 (2004), hereby incorporated herein by reference.

The principles of an electronic tongue are similar to those of the electronic nose, but the electronic tongue is designed for aqueous samples. Like the electronic nose, many of the applications of electronic tongues are related either to environmental monitoring, medical applications, or to food and beverage production. Electronic noses/tongues have been used in complex, real world environments where sensitivity as well as specificity must be considered, such as detection of chemical warfare agents, indoor air quality, and bacterial classification. See J. L. Perez Pavon, M. Del Nogal Sanchez, C. Garcia Pinto, M. Ferna Laespada B. M. Cordero and A. G. Pena, "Strategies for qualitative and quantitative analyses with mass spectrometry-based electronic noses," *Trends Anal. Chem.* 25, 257 (2006); K. Arshak, E. Moore, G. M. Lyons, J. Harris and S. Clifford, "A review of gas sensors employed in electronic nose applications," *Sens. Rev.* 24, 181 (2004); M. B. Pushkarsky, M. E. Weber, T. Macdonald and C. K. N. Patel, "High-sensitivity, high-selectivity detection of chemical warfare agents," *Appl. Phys. Lett.* 88, 044103 (2006); S. Zampolli, I. Elmi, F. Ahmed, M. Passini, G. C. Cardinali, S, Nicoletti and L. Dori, "An electronic nose based on solid state sensor arrays for low-cost indoor air quality monitoring applications," *Sens. Actuat. B* 101, 39 (2004); and R. Dutta, J. W. Gardner and E. L. Hines, "Classification of ear, nose, and throat bacteria using a neural-network-based electronic nose," *MRS Bull.* 29, 709 (2004, all of which are hereby incorporated herein by reference. An electronic tongue combines hardware, an array of electrochemical sensors, with software, automated pattern recognition algorithms such as principal component analysis, linear discriminate analysis, support vector machines, and neural networks. A set of features derived from the sensor array response is used as predictors (input), in order to predict the presence and/or concentration of analyte(s) (output). The algorithms are 'trained' using samples that include the analyte(s) of interest and potential interfering species. Training is performed automatically using multiple iterations with a large dataset to create a mathematical relationship between the features with the desired output (analyte concentrations). The pattern recognition algorithms are then tested with unknown samples to demonstrate generalization of the approach.

Most electronic tongues employ voltammetry or potentiometry with an electrode array containing either electrodes made from different materials, or different electrode coatings. See F. Winquist, C. Krantz-Rulcker and I. Lundstrom, "Electronic tongues," *MRS Bullet.* 29, 726 (2004), hereby incorporated herein by reference.

One common format for an electronic tongue is an array of ion-selective electrodes. Ion selective membranes are not 100% selective, typically suffering from interfering signals from one or more other ionic species, so the pattern recognition algorithms incorporated into an electronic tongue allow dramatic increases in both sensitivity and selectivity. However, as electronic nose/tongue technology has matured, several weaknesses have been attributed to the shortcomings of the fundamental sensor components. See F. Rock, N. Barsan and U. Weimar, "Electronic nose: Current status and future trends," *Chem. Rev.* 108, 705 (2008) hereby incorporated herein by reference.

For example, the additional information gained from adding sensor elements quickly saturates, in contrast to human sensory systems. This limits the sensitivity and selectivity that can be obtained with an electronic nose or tongue.

Bioelectronic Tongues:

Thus it has been argued that for many applications, sensitivity and selectivity can only be increased through improvements in the sensitivity and selectivity of the individual sensor elements. This approach is illustrated in the first reports of a bioelectronic tongue, in which enzymatic materials are incorporated into the individual sensor elements. See M. Gutierrez, S. Alegret and M. del Valle, "Potentiometric bioelectronic tongue for the analysis of urea and alkaline ions in clinical samples," *Biosens. Bioelectron.* 22, 2171 (2007) and M. Gutierrez, S. Alegret and M. del Valle, "Bioelectronic tongue for the simultaneous determination of urea, creatinine and alkaline ions in clinical samples," *Biosens. Bioelectron.* 23, 795 (2008), both hereby incorporated herein by reference. Determination of urea typically employs the enzyme urease, which produces ammonium ions, but selectivity is often compromised by other ionic species that interact with ammonium ion-selective electrodes. The use of a bioelectronic tongue containing an array of electrodes combined with pattern recognition rather than individual sensor elements enables the recognition of the analyte of interest amongst competing background ionic species.

The focus of this application is to make a similar advance in the selectivity of antibody electrodes. Although antibody electrodes are considerably more selective than ion-selective electrodes, they still suffer from interference arising from non-specific interactions. See J. Lahiri, L. Isaacs, J. Tien and G. M. Whitesides, "A strategy for the generation of surfaces presenting ligands for studies of binding based on an active ester as a common reactive intermediate: a surface plasmon resonance study," *Anal. Chem.* 71, 777 (1999); E. Ostuni, R. G. Chapman, R. E. Holmlin, S. Takayama and G. M. Whitesides, "A survey of structure-property relationships of surfaces that resist the adsorption of protein," *Langmuir* 17, 5605-5620, 2001; X. Qian, S. J. Metallo, I. S. Choi, H. Wu, M. N. Liang and G. M. Whitesides, "Arrays of self-assembled monolayers for studying inhibition of bacterial adhesion," *Anal. Chem.* 74, 1805 (2002); A. Bange, H. B. Halsall and W. R. Heineman, "Microfluidic immunosensor systems," *Biosens. Bioelectron.* 20, 2488 (2005) and D. R. Shankaran, V. K. Gobi and N. Miura, "Recent advancements in surface plasmon resonance immunosensors for detection of small molecules of biomedical, food and environmental interest," *Sens. Actuators B* 121, 158 (2007) all of which are hereby incorporated herein. These are typically ascribed to interactions of an antibody electrode with interfering protein species, but small molecules and ionic species may also provide interfering signals. The goal of the invention is to integrate multiple antibody electrodes into a bioelectronic tongue, and to use pattern recognition methods to discriminate the desired signal from interfering ones. The specific system to be disclosed is detection of peanut proteins, which the applicants have already demonstrated in ideal solutions using electrochemical impedance spectroscopy. (See Y. Huang, M. C. Bell and I. I. Suni, "Impedance detection of peanut protein Ara h 1," *Anal. Chem.* 80, 9157 (2008) and Y. Huang and I. I. Suni, "Degenerate Si as an electrode material for electrochemical biosensors," *J. Electrochem. Soc.* 155, J350 (2008) both hereby incorporated herein by reference.)

The "electronic fingerprint" for peanut proteins can then be determined by multivariate analysis using automated pattern recognition algorithms. (See M. L. Nogueira, R. McDonald and C. Westphal, "Can commercial peanut assay kits detect peanut allergens?," *J. AOAC Int.* 87, 1480 (2004); R. Guitierrez-Osuna, "Pattern analysis for machine olfaction," *IEEE Sens. J.* 2, 189 (2002) and S. Ampuero and J. O. Bosset, "The electronic nose applied to dairy products: A review," *Sens. Actuat. B* 94, 1 (2003) all of which are hereby incorporated herein by reference.)

To the best of the applicants' knowledge, only three research groups have reported the use of electrochemical impedance spectroscopy in an electronic tongue. (See A. Riul, R. R. Malmegrim, F. J. Fonseca and L. H. C. Mattoso, "An artificial taste sensor based on conducting polymers," *Biosens. Bioelectron.* 18, 1365 (2003); M. Ferreira, A. Riul, K. Wohnrath, F. J. Fonseca, O. N. Oliveira and L. H. C. Mattoso, "High performance taste sensor made from Langmuir-Blodgett films of conducting polymers and a ruthenium complex," *Anal. Chem.* 75, 953 (2003); A. Riul, A. M. Gallardo Soto, S. V. Mello, S. Bone, D. M. Taylor and L. H. C. Mattoso, "An electronic tongue using polypyrrole and polyaniline," *Synthet. Met.* 132, 109 (2003); D. S. dos Santos, A. Riul, R. R. Malmegrim, F. J. Fonseca, O. N. Oliveira and L. H. C. Mattoso, "A layer-by-layer film of chitosan in a taste sensor application," *Macromol. Biosci.* 3, 591 (2003); A. Riul, H. C. de Sousa, R. R. Malmegrim, D. S. dos Santos, A. C. P. L. F. Carvalho, F. J. Fonseca, O. N. Oliveira and L. H. C. Mattoso, "Wine classification by taste sensors made from ultra-thin films and using neural networks," *Sens. Actuat. B* 98, 77 (2004); C. E. Borato, F. L. Leite, L. H. C. Mattoso, R. C. Goy, S. P. Campana Filho, C. L. de Vasconcelos, C. G. da Trindade Neto, M. R. Pereira, J. L. C. Fonseca and O. N. Oliveira, "Layer-by-layer films of poly(o-ethoxyaniline), chitosan and chitosan-poly(methacrylic acid) nanoparticles and their application in an electronic tongue," *IEEE Trans. Dielect. Electr. Insul.* 13, 1101 (2006);

N. K. Wiziack, L. G. Paterno, F. J. Fonseca and L. H. C. Mattoso, "Effect of film thickness and different electrode geometries on the performance of chemical sensors made of nanostructured conducting polymer films," *Sens. Actuat. B* 122, 484 (2007); F. J. Ferreira, R. C. T. Perreira, A. C. B. Delbem, O. N. Oliveira and L. H. C. Mattoso, "Random subspace method for analyzing coffee with electronic tongue," *Electron. Lett.* 43, 1138 (2007); M. Cortina-Puig, X. Munoz-Berbel, M. del Valle, F. J. Munoz and M. A. Alonso-Lomillo, "Characterization of an ion-selective polypyrrole coating and application to the joint determination of potassium, sodium and ammonium by electrochemical impedance spectroscopy and partial least squares method," *Anal. Chim. Acta* 597, 231 (2007); M. Cortina-Pig, X. Munoz-Berbel, M. A. Alonso-Lomillo, F. J. Munoz-Pascual and M. del Valle, "EIS multianalyte sensing with an automated SIA system—An electronic tongue employing the impedimetric signal," *Talanta* 72, 774 (2007); Pioggia, G., di Francesco, F., Marchetti, A., Ferro, M., and Ahluwalia, A. A composite sensor array impedentiometric electronic tongue. Part I. Characterization. *Biosens. Bioelectron.*, 22: 2618-2623, 2007; and G. Pioggia, F. di Francesco, A. Marchetti, M. Ferro, R. Leardi and A. Ahluwalia, "A composite sensor array impedentiometric electronic tongue. Part II. Discrimination of basic tastes," *Biosens. Bioelectron.* 22, 2624 (2007) all of which are hereby incorporated herein by reference.) Another novel aspect is the use of antibodies, which do not appear to have been employed previously in an electronic tongue. Two recent reports mention the use of antibodies as sensing elements in an electronic nose, but do not actually construct such a device. (See D. D. Stubbs, S. H. Lee and W. D. Hunt, "Molecular recognition for electronic noses using surface acoustic wave sensors," *IEEE Sens. J.* 2, 294 (2002) and D. D. Stubbs, S. H. Lee and W. D. Hunt, "Investigation of cocaine plumes using surface acoustic wave immunoassay sensors," *Anal. Chem.* 75, 6231 (2003) both hereby incorporated herein by reference.

To the best of our knowledge, neither the electronic nose nor the electronic tongue has been used to detect allergens.

Impedance Detection of Peanut Proteins:

The bioelectronic tongue is for detection of a wide range of food allergens in a wide variety of food products. Much of the discussion herein is related to detection methods for peanut allergens, the technology may be applied to other allergens such as β-lactoglobulin, which is believed to be the main allergenic protein in cow's milk, and Tri a Bd 27K, which is believed to be the main allergenic protein in wheat. Requirements for food allergen biosensors include:

Sufficient sensitivity to detect trace quantities of proteins (1-100 mg/kg). (See R. Krska, E. Welzig, and S. Baumgartner, "Immunoanalytical detection of allergenic proteins in food," *Anal. Bioanal. Chem.* 378, 63 (2004) hereby incorporated herein by reference.)

Adequate specificity in complex food matrices.

Rapid, simple apparatus that can be used by inexperienced personnel.

Ideally, continuous monitoring of analytes.

The detection limit given above, which is only approximate,[34] can be translated into molarity using the density of water, yielding a detection limit ranging from $2.5 \times 10^{-8}$ to $2.5 \times 10^{-6}$ M. This compares favorably to the detection limits reported for impedance-based biosensors, which range from the nM to pM range.[35-40] A more complete bibliography of research into impedance biosensors is available in recent reviews.[41-44] Despite the excellent sensitivity of impedance biosensors, their applications have been limited so far by selectivity limitations arising from non-specific interactions.

However, by combining the use of impedance detection at antibody-coated electrodes with pattern recognition in a bioelectronic tongue constructed of many such electrodes, we remove the effect of such background interference. The main advantage of such a method relative to ELISA is the seamless ability to create a multi-analyte sensor, by including one antibody electrode for each analyte of interest. In other words, although non-specific interactions are quite complex, their complexity does not increase substantially with an increase in the number of antibody-coated electrodes; rather, an increased number of electrodes provides additional information through which the pattern recognition algorithm can achieve improved performance. The fundamental basis for detecting non-specific interactions includes the use of electrodes at which antibodies are immobilized of varying isoelectric point, and the inherent heterogeneity of protein surfaces, which already average out non-specific interactions, allowing background subtraction.

As discussed above, current methods for detecting peanut proteins are based on enzyme linked immuno-sorbent assays (ELBA),[6-9] which are time consuming, require trained personnel, are difficult to automate and miniaturize, and are not fully standardized.[10] For example, a recent study compared five different ELISA tests for peanut proteins, and these tests differ widely in their procedures, in their analytical targets, and in their performance in both biscuits and dark chocolate.[45] ELISA techniques also suffer interferences, which are often attributed to matrix effects and cross-reactivities.[46] As a result, ELISA methods suffer from false positives,[47-50] so they are often used only for preliminary screening. Another practical problem with ELISA techniques is that users typically need a separate ELISA test for each analyte of interest, as demonstrated by detection of different aflatoxins in foods.[51] The proposed bioelectronic tongue is inherently capable of multi-analyte detection through an electrode array.

Cross-reactivity of food allergens with each other, and with environmental allergens, is well-known.[52-53] Cross-reactivity is believed to arise from the existence of identical or highly similar linear or conformational epitopes in two different protein allergens. Cross-reactivity arising from pre-sensitization by a secondary protein allergen should not affect the sensor proposed here. However, the disclosed sensor may detect directly cross-reactive food and other allergens, likely resulting in a modest number of false positive results, as with other types of sensors. However, in some cases this false positive will not really be false, since many individuals will be allergic to both species anyway. It is most important that a sensor should not suffer from false negatives.

Figure 3:
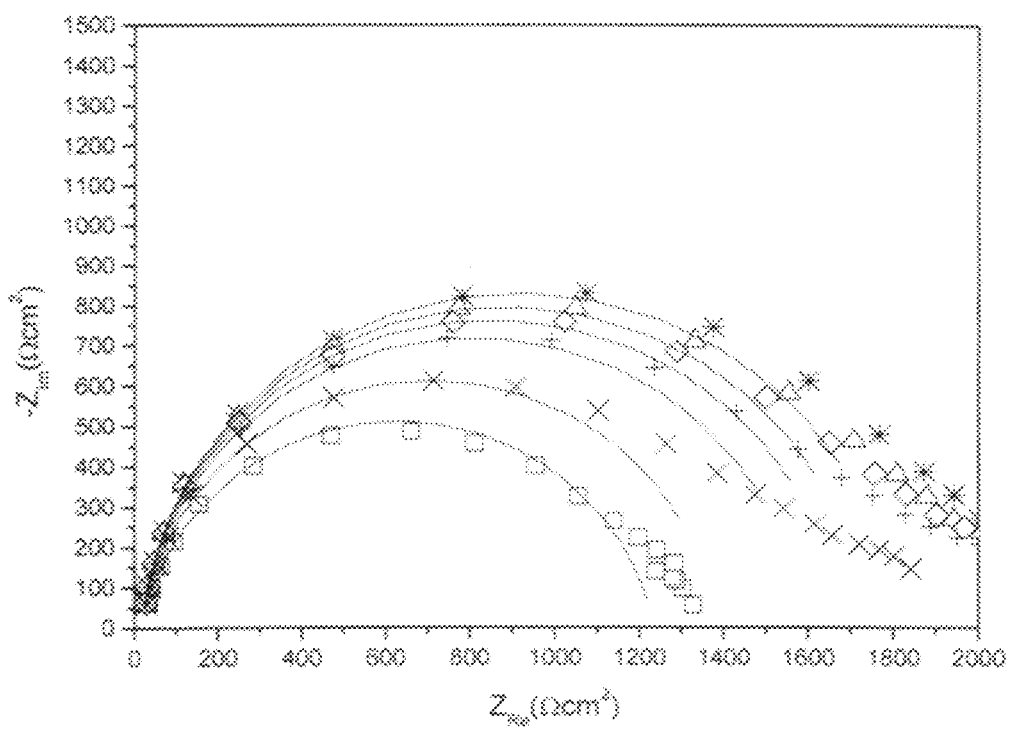
FIG. 3 illustrates the impedance response of an Au electrode with increasing concentrations of protein Ara h 1.

Results for Impedance Detection of Peanut Protein Ara h 1:

One of the applicants recently published two reports of impedance detection of peanut protein Ara h 1 after surface immobilization of its monoclonal mouse antibody onto either Au or Si electrodes.[15,16] Peanut protein Ara h 1 and its monoclonal mouse antibody were purchased from Indoor Biotechnologies. Following antibody immobilization, described later, this biosensor interface was exposed to increasing concentrations of peanut protein Ara h 1, as shown in FIG. 3. FIG. 3 illustrates an impedance response of Au electrode with increasing concentrations of peanut protein Ara h1 (from reference #15). The concentrations of Ara h1 from the innermost to the outermost semicircular arcs are 0, 0.02, 0.04, 0.08, 0.16, 0.24 µg/ml, respectively. The test solution also contains 50 mM PBS and 5 mM $Fe(CN)_6^{3-/4-}$ at pH 7.3.

Figure 4:
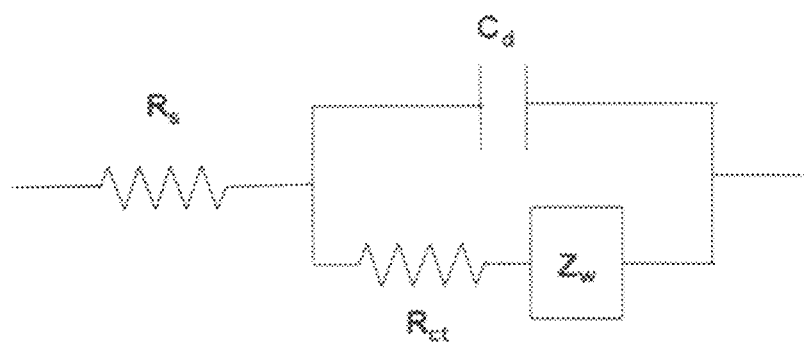
FIG. 4 illustrates a Randles type equivalent circuit.

These results are presented as a Nyquist plot, with the highest frequency at the left and the lowest frequency at the right. These results have been fit by complex nonlinear least squares (CNLS) analysis to the simplified Randles equivalent circuit model shown in FIG. 4. Here $R_S$ is the solution phase resistance, $R_{ct}$ is the charge transfer resistance, $C_d$ is the capacitance, and $Z_w$ is the Warburg impedance, which arises from mass transfer limitations and was not fit. The results of this data fit are shown in Table 1.

TABLE 1

Impedance parameters from the Randles equivalent circuit fit.

| Circuit Element | 11-MUA | 11-MUA + NHSS | 11-MUA + NHSS + anti-Ara h1 | Ara h1 protein concentration ($\mu g \cdot m^{-1}$) | | | | |
|---|---|---|---|---|---|---|---|---|
| | | | | .02 | 0.04 | 0.08 | 0.16 | 0.24 |
| $R_s$ ($\Omega \cdot cm^2$) | 3.32 | 7.74 | 16.8 | 5.0 | 16.3 | 14.9 | 15.8 | 7.2 |
| $R_{ct}$ ($\Omega \cdot cm^2$) | 2553 | 695 | 1217 | 393 | 1598 | 1693 | 1742 | 822 |
| $C_d$ ($\mu F \cdot cm^{-2}$) | 5.21 | 4.42 | 4.34 | .10 | 3.97 | 3.91 | 3.85 | 3.79 |

A clear trend of increasing charge transfer resistance ($R_{ct}$) with increasing peanut protein concentration can be observed. This corresponds approximately to the diameter of the semicircles in FIG. 3. This trend in $R_{ct}$ allows us to identify the AC probe frequencies (1-10 Hz) with the greatest sensitivity to the presence of peanut protein Ara h. At these frequencies, the response time is of the order of sec. One advantage of impedance detection is the low noise level that can be obtained even at room temperature. Although single frequency experiments were not conducted with peanut protein Ara h 1, single frequency experiments in another system yielded a noise level less than the digital increment in the analog-to-digital converter.[54]

Figure 5A:
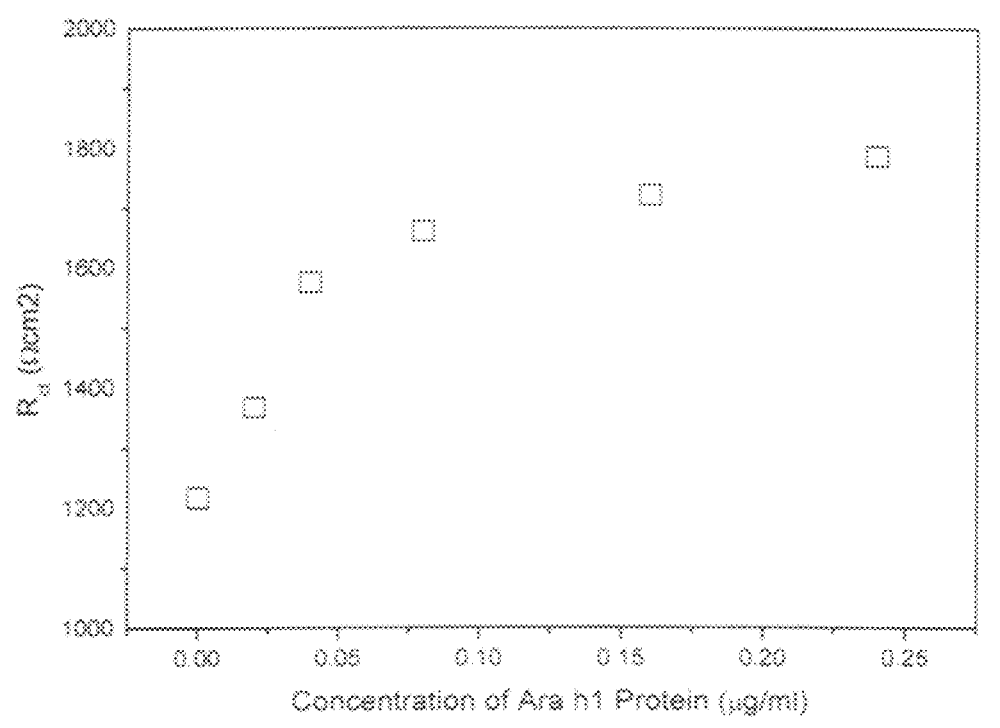
Figure 5B:
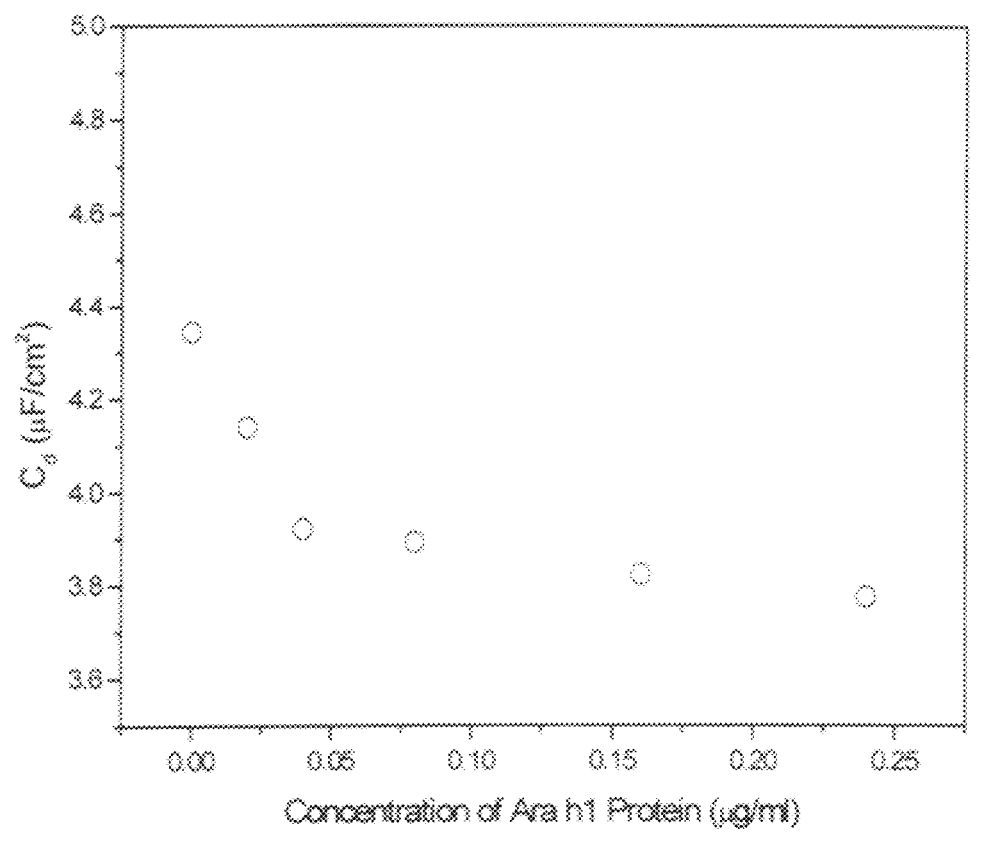

FIG. 5 illustrates the dependence of the fit impedance parameters on the concentration of peanut protein Ara h 1. In FIG. 5 the variation in the charge transfer resistance ($R_{ct}$, left side) with concentration of peanut protein Ara h 1 is illustrated. The relative change in the charge transfer resistance ($R_{ct}$) with concentration is greater than that in the differential capacitance ($C_d$). This suggests that monitoring frequencies (1-10 Hz) most sensitivity to $R_{ct}$ will yield the most sensitive detection.

Antibody Electrode Array for Bioelectronic Tongue:

The bioelectronic tongue hardware consists of an array of electrodes at which different antibodies are immobilized. This array might include the following antibodies:

Antibody to peanut protein Ara h 1, as demonstrated above.

Antibody to peanut protein Ara h 2. Since peanut proteins Ara h 1 and h2 are considered the most important food allergens, detection of both should be included in the bioelectronic tongue.

Cockroach-specific antibody from the same subtype (IgG1) as the antibodies to peanut protein Ara h 1 and Ara h 2.

Antibodies to other proteins that cause food allergies.

Antibodies to other environmental allergens not expected in food samples.

Other blank antibodies chosen to have a range of isoelectric points. If the bioelectronic tongue contains antibody electrodes with different charging behavior, then it will be more effective in discriminating between different charged or partially charged species.

As will be described later, the cockroach-specific mouse IgG1 antibody plays an important role in the development of a bioelectronic tongue, since one can assume that this antigen will not be present in food samples.[55-57] Since this antibody is also from the same mouse IgG1 sub-type as the antibodies to peanut proteins Ara h 1 and Ara h 2, this can be used as a reference element for background subtraction of non-specific interactions from the analytes of interest.[55-57] An exemplary bioelectronic tongue contains eight electrodes, as illustrated in FIG. 2, coated with the eight different antibodies: Two different target analytes, peanut proteins Ara h 1 and Ara h 2; Reference antibody from the same IgG1 sub-type, the cockroach-specific antibody; Two other food protein allergens from apple, carrot, or celery; and three other non-food protein allergens from dust mite, mold, or animal.

All antibodies can be immobilized onto an Au electrode by the following procedure:

Formation of an organic film with a carboxylate termination by immersing the Au-coated electrode into 11-mercaptoundecanoic acid (11-MUA).

Carboxylate activation by N-(3-dimethylaminopropyl)-N'-(ethylcarbodiimide hydrochloride) (EDC) and N-hydroxysulfosuccinimide sodium salt (NHSS).

Reaction of activated carboxylate groups with amine groups on the peanut protein Ara h 1 surface at pH 8, which ensures that the amine groups are deprotonated, resulting in formation of an amide bond.[58]

This technique for amide bond formation by carbodiimide coupling has become a standard method.[58] This immobilization chemistry was used for detection of peanut protein Ara h 1, as described in the above, and for other species. In some cases, this amide bond formation chemistry must be altered somewhat by varying the pH.[58] Standard methods exist for antibody immobilization onto other conductive electrode surfaces.

Reduction of Non-Specific Interactions Using Bovine Serum Albumin:

Following antibody immobilization, the electrodes are dipped in bovine serum albumin (BSA) to block the remaining active sites on the electrode, a method that has been widely employed.[59] This will likely be only partly effective, but will reduce interference effects in the bioelectronic tongue.

Reduction of Non-Specific Interactions Using Sample Dilution:

Dramatic further reduction in interfering signals is accomplished by sample dilution.[60,61] Typically, the concentration at which an antibody-based sensor exhibits a linear response is far lower than the sensitivity desired for detection of food allergens, which ranges from 1-100 µg/ml,[33] assuming that the sample density is that of water. This suggests that all liquid food matrices be strongly diluted by water by a factor of 100-1000× before being introduced into the bioelectronic tongue in order to prevent the surface immobilized antibodies from becoming saturated with peanut protein, or their corresponding antigen. Sample dilution has the added benefit of reducing the importance of non-specific interactions by that same factor of 100-1000×. Solid food matrices can be similarly diluted following dissolution into water. Sample dilution has other advantages, such as correcting for effects of varying sample viscosity and ionic strength. In other words, the properties of the testing fluid are determined largely by the dilutent.

The pattern recognition algorithms remove the remaining effects of non-specific interactions, as described below.

Pattern Recognition Algorithms Applied to Peanut Protein Detection:

Pattern recognition algorithms are applied to the bioelectronic tongue to discriminate between real detection of peanut protein and false positives. As described, an array of electrodes, as well as the patterns across frequencies generated from each electrode, creates a fingerprint for a specific analytes of interest, peanut proteins Ara h 1 and h2. The difficulty is that electrodes may also respond to other interfering species. A pattern recognition algorithm is 'trained' using data collected that includes the patterns of interest, as well as potential non-specific interactions. However, the problem diverges from a 'fingerprint' type of pattern recognition problem, in that multiple analytes of interest can be present at the same time. By including many presentations of peanut protein (with and without non-specific interactions) in the training data, the pattern recognition algorithm can learn the complex patterns. This has been demonstrated in other electronic nose/tongue applications, such as, for example in detection of chemical warfare agents in complex air environments where hundreds of gases are present of which several dozen may cause false positives.[4]

Non-specific interactions are likely to occur on multiple electrodes, whereas the peanut protein will respond only to the two electrodes with antibodies to Ara h 1 and Ara h2 proteins. Non-specific interactions may also cause changes in the frequency pattern at the peanut electrodes. Through pattern recognition, we will distinguish between these patterns through the use of the training set that includes examples of each. The bioelectronic tongue can incorporate an expected relationship between the electrode response and the concentration of peanut protein, or alternatively, the relationship can be determined phenomenologically.

For detection in only one food matrix, impedance measurements from the individual antibody electrodes are recorded in:

Dataset for Studies of One Food Matrix:
10 different cookies (prepared by the investigators to control ingredients)
Baseline measurement, plus 3 concentration levels of peanut proteins (antibodies to Ara h 1, 2) added to cookie preparation Tests are performed for each food without protein (10 tests), then repeated for 3 different concentrations (30 tests). Each measurement is made three times so to train and test the pattern recognition algorithm. Prior research suggests the use of 5-10 samples per class for training.[18,62] Models to detect the presence of peanut protein will have a binary class (that is, 30 samples without and 90 samples with protein). To detect the concentration of peanut protein, a total of four classes (three concentration levels plus one without protein) are needed, where there are 30 samples for each of the four classes. The remaining samples are used for validation and testing.

For studies of a broader range of food matrices:
Dataset for Broader Set of Food Matrices
Two additional food matrices (soup, ice cream)
10 different samples each (purchased locally)
Baseline measurement (no peanut protein), plus 3 concentration levels of peanut proteins (antibodies to Ara h 1, 2) added to cookie preparation. The three concentrations of peanut protein Ara h 1 and h2 that are tested are 0.04, 0.08 and 0.16 µg/ml, after dilution.
3 repeat experiments (above) for training and validation of models Tests without peanut protein correspond to the negative control, while the tests with known peanut protein concentrations correspond to the positive control. Negative control experiments with an additional non-peanut allergenic protein are an additional control. Tests performed for each food matrix individually (soup, ice cream), as in the cookie dataset above, first for presence of peanut protein (binary class—with or without) and then for concentration level. Lastly, data from cookies, soup, and ice cream are combined to further extend the model to more complex environments. As the complexity of the problem increases, the electrode array size may need to increase, as might the number and types of samples required to establish the pattern recognition method.

Handling of Food Matrices:

Complex pre-treatment and separation methods are typically employed when biosensors are applied to food matrices. See S. S. Haughey and G. A. Baxter, "Biosensor screening for veterinary drug residues in foodstuffs," *J. AOAC Int.* 89, 862 (2006); V. Andreu, C. Blasco and Y. Pico, "Analytical strategies to determine quinoline residues in food and the environment," *Trends Anal. Chem.* 26, 534 (2007); and C. Blasco, C. M. Torres and Y. Pico, "Progress in analysis of residual antibacterials in food," *Trends Anal. Chem.* 26, 895 (2007) all of which are hereby incorporated herein by reference. These methods can be applied to peanut protein detection according to the procedures used by those familiar in the art.

Pattern Recognition Steps:

The steps involved in pattern recognition for detection of peanut protein allergens are described in detail below. These include preprocessing, feature selection, preprocessing, performance evaluation, and validation.

Preprocessing

The preprocessing stage prepares the data for classification.[17] In this, baseline adjustment and drift compensation are performed where we consider utilizing the response to an additional reference sensor. This is an electrode that is coated with the cockroach allergen specific antibody, as described above. This reference sensor is expected to suffer the same baseline drift associated with chemically interfering species, but without any specific response to the peanut proteins of interest. The baseline of the reference can generally be subtracted, divided, or both. If drift over time is seen, then periodic recalibration can be performed and used to determine and accommodate for the drift for the sensor array.[63] One possible source of sensor drift is the presence of interfering protein species. These interactions would cause a small baseline drift which are differentiable from the response to the peanut protein.

Since the sensor output is not simply a single response, but a response versus time, the next step is a final response from this time series called compression. Two methods include utilization of the steady response to the sensor as well as transient response. In this application, we expect for simple testing setups with peanut protein only that we expect to utilize steady state response. For the case with baseline drift, even when accounted for by using a reference electrode, we can use signal processing to compute the transient response for a response that is recognized as different from drift.

Each sensor generates one or more features which are used as inputs to the pattern recognition algorithm. For impedance-based biosensors, the measurement at a sensor can be repeated for multiple frequencies. For example, in the results shown in FIG. 3, 20 points within the frequency spectrum were measured. Pattern recognition can be considered with one frequency as input to the classifier,[27, 28] with the entire spectra as input,[26] or with some portion of the spectra. Electrochemical intuition suggests that three frequencies may be sufficient, as they may contain all possible information about peanut protein binding. As described above, the two equivalent circuit elements sensitive to peanut protein binding are the charge transfer resistance (Rd) and the differential capacitance ($C_d$). Since the solution resistance is essentially constant, only two frequencies must be measured to determine $R_{ct}$ and $C_d$. However, the complex low-frequency behavior in FIG. 3 may also be sensitive to peanut protein binding, so inclusion of a third frequency might be useful. Regardless, pattern recognition is performed with additional frequencies to ensure that information is not lost. A trade-off exists with the time taken for data collection, which increases with the number of frequencies monitored, and with inclusion of low frequency data, which takes longer to acquire. The entire frequency spectrum in FIG. 3 takes about 2.5 min. to acquire.

The next step is normalization of the vector of features (measurements at multiple frequencies for each of eight sensors. One can consider normalizing the entire vector or individual sensors by utilizing the mean/std, range, or utilizing logarithmic approaches.

Feature Selection

With a large array, it may be necessary to perform feature selection or reduce the dimensionality of the data. Automated approaches for feature selection are typical next steps for large datasets. One can use standard approaches such as principle component analysis (PCA) and linear discriminate analysis (LDA) which map the multiple dimensional feature space into a projection of features ordered by variability. Typically the features with the most variability are selected as features since they carry the most information. One can also consider using random search, sequential searching, where features are added or removed to determine impact on performance, and other supervised approaches such as between-class pairwise distance, linear separability, overlapped feature histogram, hill climbing, simulated annealing, threshold accepting optimization, and expectation maximization.[64]

As an example we have an array of two peanut biosensors, combined with other six other protein biosensors. The additional array elements are used to capture information on non-specific interactions. Since the biosensor array contains only eight sensors, our feature set may not require reduction and the features could be used directly. One can expand our feature set by considering the detailed impedance spectra and the inclusion of additional frequencies. This may increase the feature set, provide more information to allow for separation, and potentially require feature selection.

Classification

Pattern recognition is a mature field in electrical and computer engineering and computer science. A variety of pattern recognition tools have been developed and utilized for many applications where simple thresholds achieve poor performance. One of the chief advantages of many pattern recognition tools is that they can create non-linear thresholds to separate features in multi-dimensional feature space and these non-linear models can be determined automatically through the use of a training set.

To develop a pattern recognition algorithm, we divide the data into a training, test, and validation sets. The training set is used to create the model and select the thresholds. This is usually an iterative process where weights/model is updated to minimize the classification error. A test set is used to verify that the model will generalize to an unseen dataset. Once the model is selected based on the training/test stages, the validation set provides final evidence that the model will be successful in the device's application. The main requirement for automated supervised pattern recognition is data that represents the variability likely to been seen in a given problem and that has enough examples available. Initially, since the dataset is small, one would use cross-validation, where a small set is withheld for validation while the remaining data is used for training/testing. The process is repeated many times (100× or more) repeatedly on small subsets of the data and the average results are used to estimate the predicted performance of the classifier on an unseen data set.

One may consider multiple pattern recognition models, including artificial neural networks, support vector machines, classification trees, and nearest neighbor classifiers. Most of these have been applied to electronic nose and tongue applications.[21, 26, 65] Each has their own advantages and disadvantages. Supervised feedforward neural networks, called Multilayer perceptrons, are trained with the standard back-propagation algorithm.[66] Nearest neighbor classifier using a training set of both positive and negative cases performs classification by calculating the normalized Euclidean distance to the nearest training case.[67] Classification trees derive a sequence of if-then-else rules using the training set in order to assign a class label to the input data.[68] Lastly, support vector machines (SVM) map input vectors to a higher dimensional space where a maximal separating hyperplane is constructed.[69] By using the cross-validation approach across the models described above, the approximate performance can be estimated for a particular pattern recognition problem. One would also consider factors such as overfitting, model order selection, early stopping, and regularization.[7]

Performance Evaluation of Bioelectronic Tongue

The aim of the method and device is to detect the presence or absence of peanut protein above a specific minimum concentration. In this case, the classes are presence of peanut protein or not, i.e. a binary classification problem (0, 1). Additionally the method and device will further assess the pattern of the features in order to relate the magnitude to concentration. In this case, the 'classes' to be detected would be level of concentration where the classes would increase according to the desired concentration resolution.

Validation Plan

The algorithms developed above are only as good as the data used to train them. Each component can be developed and considering the impact of different preprocessing, feature selection, and classification algorithms. However, its development is iterative as the data becomes available.

Considerations for Commercialization:

The applicants suggest a point-of-use biosensor for detecting peanut protein allergen. The following practical requirements must also be considered:

Rapidity of the overall testing process.

Portability, possibly including miniaturization of all components.

Regeneration of the biosensor interface between sample tests.

Rapidity of the Testing Process:

For the chemical part of this method and device, sensor, antibody-antigen interactions are quite rapid, and do not slow detection of peanut protein. Impedance detection of peanut protein Ara h 1 is most sensitive at frequencies of 1-10 Hz. At such frequencies, impedance detection is quite rapid, and the slowest chemical step is mass transfer. With a well designed fluid handling system, the time response is on the order of seconds. The time response of the pattern recognition algorithms is expected to be within 0.5 second or much less and is not a limiting factor.

The sample dilution step discussed above will of course slow the response time somewhat. However, dilution is a relatively simple process, and there are several ways in which this can accomplished rapidly. For example, if the sensor electrodes are stored in an aqueous solution, the analyte can be introduced into that pre-existing aqueous solution as only a small volume, maintaining the dilution factor give above of 100-1000×. Mixing could also be accomplished using short bursts of acoustic energy, for example.

Miniaturization:

The electrochemical detection system is relatively easy to miniaturize. If one takes apart conventional potentiostats and impedance analyzers, they are essentially a collection of integrated circuits. As semiconductor electronics are continuously made faster and smaller, the price and the quality of "electrochemistry-on-a-chip" is continuously improving. The remainder of the detection process involves reagent mixing and reagent transport, which are easily handled, for example, within lab-on-a-chip technologies.

Regeneration of the Biosensor Interface:

Regeneration of ELISA and other immunosensors can allow reuse for 50-60 cycles and is typically achieved by introduction of a chaotropic agent, often an acidic or basic solution.[70] This is as effective for an impedance biosensor as for traditional ELISA tests. In addition, one can anticipate multiplexing between many sensor electrodes since they are constructed out of inexpensive starting materials.

As discussed above, even though peanut allergens have been the main focus of this application, the concepts and techniques presented are applicable to other food allergens, so this application is not limited to peanut allergens. Many variations and modifications may be made to the preferred embodiments of the disclosure as describe above. All such modifications and variations are intended to be herein within the scope of the present invention. It is therefore wished to have it understood that the present invention should not be limited in scope, except by the terms of the following claims.

REFERENCES

The following references are hereby incorporated in their entirety herein by reference.

1. S. A. Bock, "Prospective appraisal of complaints of adverse reactions to foods in children during the first three years of life," *Pediatrics* 79, 683 (1987).
2. W. Burks, G. A. Bannon, S. Sicherer and H. A. Sampson, "Peanut-induced anaphylactic reactions," *Inter. Arch. Allergy Immunol.* 119, 165 (1999).
3. T. J. Furlong, J. DeSimone and H. Sicherer, "Peanut and tree nut allergic reactions in restaurants and other food establishments," *J. Allergy Clin. Immunol.* 108, 867 (2001).
4. G. W. Palmer, D. A. Dibbern, A. W. Burks, G. A. Bannon, S. A. Bock, H. S. Porterfield, R. A. McDermott and S. C. Dreskin, "Comparative potency of Ara h1 and Ara h 2 in immunochemical and functional assays of allergenicity," *Clin. Immunol.* 115, 302 (2005).
5. A. Barre, J. P. Borges, R. Culerrier, and P. Rouge, "Homology modeling of the major peanut allergen Ara h 2 and surface mapping of IgE-binding epitopes," *Immunol. Lett.* 100, 153 (2005).
6. A. Pomes, R. M. Helm, G. A. Bannon, A. W. Burks, A. Tsay and M. D. Chapman, "Monitoring peanut allergen in food products by measuring Ara h 1," *J. Allergy Clin. Immunol.* 111, 640 (2003).
7. M. L. Nogueira, R. McDonald and C. Westphal, "Can commercial peanut assay kits detect peanut allergens?," *J. AOAC Int.* 87, 1480 (2004).
8. D. A. Schmitt, H. Cheng, S. J. Maleki and A. W. Burks, "Competitive inhibition ELISA for quantification of Ara h 1 and Ara h 2, the major peanut allergens," *J. AOAC Int.* 87, 1492 (2004).
9. M. Kiening, R. Niessner, E. Drs, S. Baumgartner, R. Krska, M. Bremer, V. Tomkies, P. Reece, C. Danks, U. Immer and M. G. Weller, "Sandwich immunoassays for the determination of peanut and hazelnut traces in foods," *J. Agric. Food Chem.* 53, 3321 (2005).
10. A. L. Ghindilis, P. Atanasov, M. Wilkins and E. Wilkins, "Immunosensors: Electrochemical sensing and other engineering approaches," *Biosens. Bioelectron.* 13, 113 (1998).
11. I. Mohammed, W. M. Mullett, E. P. C. Lai and J. J. Yeung, "Is biosensor a viable method for food allergen detection?" *Anal. Chim. Acta* 444, 97 (2001).
12. M. T. Veledo, M. de Frutos and J. C. Diez-Masa, "Analysis of trace amounts of bovine β-lactoglobulin in infant formulas by capillary electrophoresis with on-capillary derivatization and laser-induced fluorescence detection," *J. Separ. Sci.* 28, 941 (2005).
13. K. J. Shefcheck and S. M. Musser, "Confirmation of the allergenic peanut protein, Ara h 1, in a model food matrix using liquid chromatography/tandem mass spectrometry (LC/MS/MS)," *J. Agric. Food Chem.* 52, 2785 (2004).
14. H. Huang, P. Ran and Z. Liu, "Impedance sensing of allergen-antibody interaction on glassy carbon electrode modified by gold electrodeposition," *Bioelectrochemistry* 70, 257 (2007).
15. Y. Huang, M. C. Bell and I. I. Suni, "Impedance detection of peanut protein Ara h 1," *Anal. Chem.* 80, 9157 (2008).
16. Y. Huang and I. I. Suni, "Degenerate Si as an electrode material for electrochemical biosensors," *J. Electrochem. Soc.* 155, J350 (2008).

17. R. Guitierrez-Osuna, "Pattern analysis for machine olfaction," *IEEE Sens. J.* 2, 189 (2002).
18. S. Ampuero and J. O. Bosset, "The electronic nose applied to dairy products: A review," *Sens. Actual. B* 94, 1 (2003).
19. A. Riul, R. R. Malmegrim, F. J. Fonseca and L. H. C. Mattoso, "An artificial taste sensor based on conducting polymers," *Biosens. Bioelectron.* 18, 1365 (2003).
20. M. Ferreira, A. Riul, K. Wohnrath, F. J. Fonseca, O. N. Oliveira and L. H. C. Mattoso, "High performance taste sensor made from Langmuir-Blodgett films of conducting polymers and a ruthenium complex," *Anal. Chem.* 75, 953 (2003).
21. A. Riul, A. M. Gallardo Soto, S. V. Mello, S. Bone, D. M. Taylor and L. H. C. Mattoso, "An electronic tongue using polypyrrole and polyaniline," *Synthet. Met.* 132, 109 (2003).
22. D. S. dos Santos, A. Riul, R. R. Malmegrim, F. J. Fonseca, O. N. Oliveira and L. H. C. Mattoso, "A layer-by-layer film of chitosan in a taste sensor application," *Macromol. Biosci.* 3, 591 (2003).
23. A. Riul, H. C. de Sousa, R. R. Malmegrim, D. S. dos Santos, A. C. P. L. F. Carvalho, F. J. Fonseca, O. N. Oliveira and L. H. C. Mattoso, "Wine classification by taste sensors made from ultra-thin films and using neural networks," *Sens. Actuat. B* 98, 77 (2004).
24. C. E. Borato, F. L. Leite, L. H. C. Mattoso, R. C. Goy, S. P. Campana Filho, C. L. de Vasconcelos, C. G. da Trindade Neto, M. R. Pereira, J. L. C. Fonseca and O. N. Oliveira, "Layer-by-layer films of poly(o-ethoxyaniline), chitosan and chitosan-poly(methacrylic acid) nanoparticles and their application in an electronic tongue," *IEEE Trans. Dielect. Electr. Insul.* 13, 1101 (2006).
25. N. K. Wiziack, L. G. Paterno, F. J. Fonseca and L. H. C. Mattoso, "Effect of film thickness and different electrode geometries on the performance of chemical sensors made of nanostructured conducting polymer films," *Sens. Actual. B* 122, 484 (2007).
26. F. J. Ferreira, R. C. T. Perreira, A. C. B. Delbem, O. N. Oliveira and L. H. C. Mattoso, "Random subspace method for analyzing coffee with electronic tongue," *Electron. Lett.* 43, 1138 (2007).
27. M. Cortina-Puig, X. Munoz-Berbel, M. del Valle, F. J. Munoz and M. A. Alonso-Lomillo, "Characterization of an ion-selective polypyrrole coating and application to the joint determination of potassium, sodium and ammonium by electrochemical impedance spectroscopy and partial least squares method," *Anal. Chim. Acta* 597, 231 (2007).
28. M. Cortina-Pig, X. Munoz-Berbel, M. A. Alonso-Lomillo, F. J. Munoz-Pascual and M. del Valle, "EIS multianalyte sensing with an automated SIA system—An electronic tongue employing the impedimetric signal," *Talanta* 72, 774 (2007).
29. Pioggia, G., di Francesco, F., Marchetti, A., Ferro, M., and Ahluwalia, A. A composite sensor array impedentiometric electronic tongue. Part I. Characterization. *Biosens. Bioelectron.*, 22: 2618-2623, 2007.
30. G. Pioggia, F. di Francesco, A. Marchetti, M. Ferro, R. Leardi and A. Ahluwalia, "A composite sensor array impedentiometric electronic tongue. Part II. Discrimination of basic tastes," *Biosens. Bioelectron.* 22, 2624 (2007).
31. D. D. Stubbs, S. H. Lee and W. D. Hunt, "Molecular recognition for electronic noses using surface acoustic wave sensors," *IEEE Sens. J.* 2, 294 (2002).
32. D. D. Stubbs, S. H. Lee and W. D. Hunt, "Investigation of cocaine plumes using surface acoustic wave immunoassay sensors," *Anal. Chem.* 75, 6231 (2003).
33. R. Krska, E. Welzig, and S. Baumgartner, "Immunoanalytical detection of allergenic proteins in food," *Anal. Bioanal. Chem.* 378, 63 (2004).
34. R. W. R. Crevel, B. K. Ballmer-Weber, T. Holzhauser, J. O. B. Hourihane, A. C. Knulst, A. R. Mackie, F. Timmermans and S. L. Taylor, "Thresholds for food allergens and their value to different stakeholders," *Allergy* 63, 597 (2008).
35. C. Berggren and G. Johansson, "Capacitance of antibody-antigen interaction in a flow system," *Anal. Chem.* 69, 3651 (1997).
36. V. M. Mirsky, M. Riepl and O. S. Wolfbeis, "Capacitive monitoring of protein immobilization and antigen-antibody reactions on monomolecular alkylthiol films on gold electrodes," *Biosens. Bioelectron.* 12, 977 (1997).
37. M. Zayats, O. A. Raitman, V. I. Chegel, A. B. Kharitonov and I. Willner, "Probing antigen-antibody binding processes by impedance measurements on ion-sensitive field effect transistor devices and complementary surface plasmon resonance analyses: Development of cholera toxin sensors," *Anal. Chem.* 74, 4763 (2002).
38. Y. Xu, Y. Jiang, H. Cai, P. G. He and Y. Z. Fang, "Electrochemical impedance detection of DNA hybridization based on the formation of M-DNA on polypyrrole/carbon nanotubes modified electrode," *Anal. Chim. Acta* 516, 19 (2004).
39. F. Lucarelli, G. Marrazza and M. Mascini, "Enzyme-based impedimetric detection of PCR products using oligonucleotide-modified screen-printed gold electrodes," *Biosens. Bioelectron.* 20, 2001 (2005).
40. H. Cai, T. M. H. Lee and I. M. Hsing, "Label-free protein recognition using an aptamer-based impedance measurement assay," *Sens. Actuators B* 114, 433 (2006).
41. E. Katz and I. Willner, "Probing biomolecular interactions at conductive and semiconductive surfaces by impedance spectroscopy: Routes to impedimetric immunosensors, DNA-sensors, and enzyme biosensors," *Electroanalysis* 15, 913 (2003).
42. J. G. Guan, Y. Q. Miao and Q. J. Zhang, "Impedimetric biosensors," *J. Biosci. Bioeng.* 97, 219 (2004).
43. B. Pejcic and R. DeMarco, "Impedance spectroscopy: Over 35 years of electrochemical sensor optimization," *Electrochim. Acta* 51, 6217 (2008).
44. L. Yang and R. Bashir, "Electrical/electrochemical impedance for rapid detection of foodborne pathogenic bacteria," *Biotechnol. Adv.* 26, 135 (2008).
45. R. E. Poms, M. E. Agazzi, A. Bau, M. Brohee, C. Capelletti, J. V. Norgaard and E. Anklam, "Inter-laboratory validation study of five commercial ELISA test kits for the determination of peanut proteins in biscuits and dark chocolate," *Food Additives Contamin.* 22, 104 (2005).
46. G. S, Nunes, L. A. Toscano and D. Barcelo, "Analysis of pesticides in food and environmental samples by enzyme-linked immunosorbent assays," *Trends Anal. Chem.* 17, 79 (1998).
47. J. L. Ferreira, S. Maskanka, E. Johnson and M. Goodnough, "Detection of botulinal neurotoxins A, B, E, and F by amplified enzyme-linked immunosorbent assay: Collaborative study," *J. AOAC Int.* 86, 314 (2003).
48. K. Sasaki, T. R. Glass and N. Ohmura, "Validation and accuracy of enzyme-linked immunosorbent assay in hybridoma screening and proposal of an improved screening method," *Anal. Chem.* 77, 1933 (2005).
49. D. Knopp, M. Seifert, V. Vaananen and R. Niessner, "Determination of aromatic polycyclic hydrocarbons in contaminated soil and water by immunological and chromatographic methods," *Environ. Sci. Technol.* 34, 2035 (2000).
50. H. Jiang, C. Adams, N. Graziano, A. Roberson, M. McGuire and D. Khiari, "Enzyme-linked immunosorbent assay (ELISA) of atrizine in raw and finished drinking water," *Environ. Engin. Sci.* 23, 357 (2006).
51. K. E. Sapsford, M. M. Ngundi, M. H. Moore, M. E. Lassman, L. C. Shriver-Lake, C. R. Tatt and F. S. Ligler, "Rapid detection of foodborne contaminants using an array biosensor," *Sens. Actual. B* 113, 599 (2006).
52. R. C. Aalberse, J. H. Akkerdaas and R. van Ree, "Cross-reactivity of IgE antibodies to allergens," *Allergy* 56, 478 (2001).
53. H. Breiteneder and C. Mills, "Structural bioinformatic approaches to understand cross-reactivity," *Mol. Nutr. Food Res.* 50, 628 (2006).
54. J. Wang, K. A. Carmon, L. A. Luck and I. I. Suni, "Electrochemical impedance biosensor for glucose detection utilizing a periplasmic *E. coli* receptor protein," *Electrochem. Solid-state Lett.* 8, H61 (2005).
55. D. G. Bracewell, A. Gill and M. Hoare, "An in-line flow injection optical biosensor for real-time bioprocess monitoring," *Trans. IChemE* 80C, 71 (2002).
56. A. N. Naimushin, S. D. Soelberg, D. U. Bartholomew, J. L. Elkind and C. E. Furlong, "A portable surface plasmon resonance (SPR) sensor system with temperature regulation," *Sens. Actual. B* 96, 253 (2003).
+57. H. Baac, J. P. Hajos, J. Lee, D. Kim, S. J. Kim and M. L. Shuler, "Antibody-based surface plasmon resonance detection of intact viral pathogen," *Biotechnol. Bioengin.* 94, 815 (2006).
58. B. Johnsson, S. Lofas and G. Lindquist, "Immobilization of proteins to a carboxymethyldextran-modified gold surface for biospecific interaction analysis in surface plasmon resonance sensors," *Anal. Biochem.* 198, 268 (1991).
59. D. R. Sankaran, K. V. Gobi and N. Miura, "Recent advancements in surface plasmon resonance immunosensors for detection of small molecules of biomedical, food and environmental interest," *Sens. Actuat. B* 121, 158 (2007).
60. K. Gaus and E. A. H. Hall, "Surface Plasmon resonance sensor for heparin measurements in blood plasma," *Biosens. Bioelectron.* 13, 1307 (1998).
61. L. I. Andersson, E. Hardenborg, M. Sandberg-Stall, K. Moller, J. Henriksson, I. Bramsby-Sjostrom, L. I. Olsson and M. Abdel-Rahim, "Development of a molecularly imprinted polymer based solid-phase extraction of local anaesthetics from human plasma," *Anal. Chim. Acta* 526, 147 (2004).
62. M. Pardo and G. Sberveglieri, "Remarks on the Use of Multilayer Perceptrons for the Analysis of Chemical Sensor Array Data," *IEEE Sens. J.* 4, 355 (2004).
63. F. Javier Acevedo, A. Narvaez, S. Maldonado, P. Siegmann, S. Lafuente and H. Gómez, "Signal preprocessing techniques for an electronic tongue," *Proceedings of the 5th WSEAS Int. Conf. on Signal Processing, Computational Geometry & Artificial Vision*, Malta, Sep. 15-17, 2005, 15-20 (2005).
64. D. Zongker and A. Jain, "Algorithms for feature selection: An evaluation," *Proceedings of the 13th International Conference on Pattern Recognition*, 18-22 (1996).
65. C. Apetrei, I. M. Apetrei, I. Nevares, M. Del Alamo, V. Parra, M. L. Rodriguez-Mendez and J. A. De Saja, "Using an e-tongue based on voltammetric electrodes to discriminate among red wines aged in oak barrels or aged using alternative methods Correlation between electrochemical signals and analytical parameters," *Electrochimica Acta* 52, 2588 (2007).
66. J. C. Principe, N. R. Euliano and W. C. Lefebvre, *Neural and Adaptive Systems*, Wiley, New York, 2000.
67. D. Aha and D. Kibler, "Instance-based learning algorithms," *Machine Learning* 6, 37 (1991).
68. R. Quinlan, "C4.5: Programs for Machine Learning," Morgan Kaufmann Publishers, San Mateo, Calif., 1993.
69. J. Platt, "Fast Training of Support Vector Machines using Sequential Minimal Optimization," Chap. 12, in *Advances in Kernel Methods—Support Vector Learning*, B. Scholkopf, C. Burges, and A. Smola, eds., pp. 185-208, MIT Press, (1999).
70. J. W. Chung, S. D. Kim, R. Bernhardt and J. C. Pyun, "Additive assay for the repeated measurements of immunosensor without regeneration step," *Sens. Actual. B* 114, 1007 (2006), and references therein.

We claim:
1. A method of detecting food allergens comprising the acts of:
providing one or more water diluted food sample(s);
making said sample(s) part of a sensor array;
sampling said samples using an electrical (non-magnetic) impedance analyzer, which includes an array of antibody-coated electrodes, some serving as measurements electrodes, at which the antibody to a food allergen is immobilized, and some serving as control electrodes, at which reference antibodies are immobilized for subtraction background of non-specific interaction, wherein the reference antibodies having different isoelectric point ranging from 5-9;
providing an electrical output from said analyzer to a preprocessing portion;
selecting data from said preprocessing portion for a feature reaction portion;
providing data from said feature reaction portion to a pattern recognition portion including a training set, a test set and a validation set that determines the concentration of a food allergen within said sample, wherein said training set comprises the acts of creating a model and selecting threshold; wherein said training set is an iterative process where weights/models are updated to minimize classification errors; wherein said test set verifies said training model; wherein said validation set uses cross-validation, wherein a small set is withheld for validation while the remaining data is used for training/testing.
2. The method of claim 1 comprising the acts of:
applying an AC probe voltage to said array and measuring the current response;
fitting an equivalent circuit to said current response;
determining the components of said array using a Randles circuit for such analysis;
graphing imaginary (out of phase) versus the real (in phase) electric impedance values;
plotting a Nyquist plot of said impedance values, and selecting the frequencies most sensitive to binding of food allergens;
using pattern recognition to determine the presence of an allergen and using a display device to report the presence of said allergen.
3. The method of claim 1 wherein said array includes one or more antibodies selected from a group consisting of:
mouse monoclonal antibody to peanut protein Ara h 1;
mouse monoclonal antibody to peanut protein Ara h 2;

Cockroach-specific mouse monoclonal antibody from the same subtype (lgG 1) as the antibodies to peanut protein Ara h 1 and Ara h 2;
monoclonal or polyclonal antibodies to other proteins known to cause food allergies;
monoclonal or polyclonal antibodies to other environmental allergens not expected in food samples; and
other reference monoclonal or polyclonal antibodies chosen to have a range of isoelectric points wherein having antibody electrodes with different charging behavior then said array will be more effective.

4. The method of claim 1 comprising the acts of:
immobilizing antibodies onto a biocompatible electrode, wherein said electrodes are selected from a group consisting of Au, Si, Pt, and some form of C, by antibody immobilization onto said electrode surface.

5. The method of claim 1 comprising the acts of:
dipping said antibody immobilized electrodes in bovine serum albumin (BSA) to block any remaining active sites on said electrode thus reducing interference effects.

6. The method of claim 1 comprising the acts of:
using sample water dilution by a factor of 10 to 10,000 times to reduce non-specific interactions.

7. The method of claim 1 further comprising:
displaying said concentration of said allergen within said sample of interest.

8. The method of claim 1 further comprising:
using a set of features derived from said impedance analyzer response as predictors, in order to predict a presence and/or concentration of analyte(s).

9. The method of claim 8 further comprising the acts of:
training a set of algorithms using samples including analyte(s) of interest and potential interfering species, wherein said training is performed automatically using multiple iterations with a large dataset to create a mathematical relationship between features with a desired output of analyte concentrations
wherein said training is performed with said pattern recognition portion.

10. The method of claim 4 wherein a set of pattern recognition algorithms are tested with said unknown samples.

11. The method of claim 4 comprising the acts of:
using a bioelectronic tongue having an array of electrodes combined with said pattern recognition enabling recognition of an analyte of interest amongst competing background species.

12. The method of claim 1 comprising the acts of: using impedance detection of antibody-coated electrodes;
using said pattern recognition within a bioelectronic tongue constructed of many such electrodes, wherein such a combination removes an effect of background interference and antibody cross-reactivity.

13. The method of claim 11 comprising the act of:
including one antibody electrode for each analyte of interest wherein an increase in the number of antibody-coated electrodes provides additional information through which a pattern recognition algorithm achieves improved performance.

14. The method of claim 1 comprising the acts of:
detecting non-specific interactions including a use of electrodes within said sensor array that includes immobilized antibodies with isoelectric points that range from 5-9; and
antibodies with different isoelectric points will have different behavior in terms of non-specific adsorption.

15. The method of claim 1 comprising the act of:
using an array of electrodes at which different antibodies are immobilized.

16. The method of claim 1 comprising the acts of:
fitting results from a detection array that has been exposed to increasing concentrations of food allergens by a complex nonlinear least squares analysis;
coupling said fitted results to a Randles equivalent circuit model wherein Rs is a solution phase resistance, Rct is a charge transfer resistance, Cd is a capacitance and Zw is a Warburg impedance.

17. The method of claim 16 comprising the acts of:
observing a clear trend of increasing charge transfer resistance (Re) with increasing peanut protein concentration wherein a trend in said Rct allows identification of AC probe frequencies with a greatest sensitivity to presence of a peanut protein Ara h 1, or other food allergens.

18. The method of claim 17 wherein said probe frequencies are expected to be in the range 1 to 10 Hz, but may include other frequencies as well.

19. The method of claim 1 wherein a response time of allergen detection is of the order of seconds.

20. The method of claim 1 comprising the acts of:
immobilizing antibodies onto a biocompatible electrode, wherein said electrodes are selected from a group consisting of Au, Si, Pt, and some form of C, by protein immobilization onto said electrode surface.

21. The method of claim 20 further comprises the acts of:
using an Au electrode(s);
forming an organic film with a carboxylate termination by immersing said Au electrode into 11-mercaptoundecanoic acid (11-MUA);
activating carboxylate groups by N-(3-dimethylaminopropyl)-N'-(ethylcarbodiimide hydrochloride) (EDC) and N-hydroxysulfosuccinimide sodium salt (NHSS); and
reacting activated carboxylate groups with amine groups on a peanut protein Ara h 1 surface at pH 8, thus ensuring that the amine groups are deprotonated, resulting in formation of an amide bond.

22. The method of claim 1 comprising the acts of:
dipping antibody immobilized electrodes in bovine serum albumin (BSA) to block any remaining active sites on said electrode thus reducing interference effects.

23. The method of claim 1 comprising the acts of:
applying an AC probe voltage to an electrochemical system and measuring the current response;
fitting an equivalent circuit to the chemical reaction; determining the components of said circuit;
using a Randles circuit for such analysis;
selecting the frequencies most sensitive to binding of food allergens;
performing pattern recognition process that determines the concentration of a food allergen within said sample;
displaying and reporting the presence of an allergen.

24. The method of claim 1 comprising the acts of:
applying an AC probe voltage to said array and measuring the current response; fitting an equivalent circuit to said current response;
graphing imaginary (out of phase) versus the real (in phase) electric impedance values;
plotting a Nyquist plot of said impedance values, and selecting the frequencies most sensitive to binding of food allergens;
using pattern recognition to determine the presence of an allergen and using a display device to report the presence of said allergen.

25. The method of claim 4 further comprising:

using an Au electrode;

forming an organic film with a carboxylate termination by immersing said electrode into 11-mercaptoundecanoic acid (11-MUA);

activating carboxylate groups by immersion into N-(3-dimethylaminopropyl)-N'-(ethylcarbodiimide hydrochloride) (EDC) and N-hydroxysulfosuccinimide sodium salt (NHSS);

reacting activated carboxylate groups with amine groups on antibody surface at pH 8, thus ensuring that the amine groups are deprotonated, resulting in formation of an amide bond; and other bioelectronic electrodes would use a similar procedure.

26. The method of claim 1 wherein said training set includes samples with increasing concentrations of the different food allergens.

\* \* \* \* \*